United States Patent
Bachmeir et al.

(10) Patent No.: US 9,744,623 B2
(45) Date of Patent: Aug. 29, 2017

(54) DEVICE AND METHOD FOR SEPARATING A LONGITUDINALLY-EXTENDED CYLINDRICAL WORKPIECE

(71) Applicant: ROFIN-BAASEL LASERTECH GMBH & CO. KG, Starnberg (DE)

(72) Inventors: Johannes Bachmeir, Penzing (DE); Dieter Pankatz, Gauting (DE); Andreas Glaser, Gauting (DE)

(73) Assignee: ROFIN-BAASEL Lasertech GmbH & Co. KG, Starnberg (DE)

( * ) Notice: Subject to any disclaimer, the term of this patent is extended or adjusted under 35 U.S.C. 154(b) by 420 days.

(21) Appl. No.: 14/583,987

(22) PCT Filed: May 16, 2013

(86) PCT No.: PCT/EP2013/060143
§ 371 (c)(1),
(2) Date: Dec. 29, 2014

(87) PCT Pub. No.: WO2014/000965
PCT Pub. Date: Jan. 3, 2014

(65) Prior Publication Data
US 2015/0290743 A1  Oct. 15, 2015

(30) Foreign Application Priority Data

Jun. 28, 2012 (DE) .......... 10 2012 211 206
Jul. 19, 2012 (DE) .......... 10 2012 212 718

(51) Int. Cl.
*B23K 26/142* (2014.01)
*B23K 26/38* (2014.01)
(Continued)

(52) U.S. Cl.
CPC .......... *B23K 26/16* (2013.01); *B23K 26/0823* (2013.01); *B23K 26/0846* (2013.01);
(Continued)

(58) Field of Classification Search
CPC ........ B23K 26/14; B23K 26/16; B23K 26/38; B23K 26/30; B23K 26/422; B23K 26/0846; B23K 37/0533
(Continued)

(56) References Cited

U.S. PATENT DOCUMENTS 5,852,277 A    12/1998  Gustafson
6,612,012 B2 *  9/2003  Mitelberg ................. A61F 2/91
                                                148/426

(Continued)

FOREIGN PATENT DOCUMENTS

DE    102008011232 A1    8/2008
DE    102007018537 A1   10/2008

*Primary Examiner* — Samuel M Heinrich
(74) *Attorney, Agent, or Firm* — Laurence A. Greenberg; Werner H. Stemer; Ralph E. Locher

(57) ABSTRACT

In a device for separating a longitudinally-extended cylindrical workpiece, which has a diameter in the sub-millimeter range, into individual segments, the workpiece is guided in a clamping device. The clamping device includes a first and a second clamping jaw and a feed opening for the workpiece. The feed opening is fitted between the clamping jaws on the side facing the other clamping jaw and a longitudinal groove which defines a direction of advancement of the workpiece for receiving and guiding the workpiece between the clamping jaws. The clamping device has a passage for a laser beam and a cutting gas, which passage defines a working zone, disrupts the longitudinal groove and runs parallel thereto. A cutter head is arranged in the working zone and has an outlet opening for the laser beam and the cutting gas, which outlet opening is aligned with the passage.

10 Claims, 2 Drawing Sheets

(51) Int. Cl.
    *B23K 37/04*     (2006.01)
    *B23K 26/16*     (2006.01)
    *B23K 37/053*    (2006.01)
    *B23K 26/08*     (2014.01)
    *B23K 26/70*     (2014.01)
    *B23K 26/146*    (2014.01)
    *B23K 26/40*     (2014.01)
    *B23K 26/402*    (2014.01)
    *A61F 2/86*      (2013.01)
    *B23K 101/06*    (2006.01)
    *B23K 103/08*    (2006.01)
    *B23K 103/00*    (2006.01)

(52) U.S. Cl.
    CPC ............ *B23K 26/146* (2015.10); *B23K 26/38* (2013.01); *B23K 26/40* (2013.01); *B23K 26/402* (2013.01); *B23K 26/702* (2015.10); *B23K 37/0533* (2013.01); *A61F 2/86* (2013.01); *B23K 2201/06* (2013.01); *B23K 2203/08* (2013.01); *B23K 2203/42* (2015.10)

(58) Field of Classification Search
    USPC ............ 219/121.67–121.72, 121.82, 121.84; 29/557; 264/400
    See application file for complete search history.

(56)  References Cited

U.S. PATENT DOCUMENTS

2003/0234242 A1    12/2003   McCoy
    2005/0049579 A1     3/2005   Shedlov et al.
    2009/0151147 A1*    6/2009   Bialas ................... B23K 26/16
                                                             29/557
    2013/0137059 A1*    5/2013   Jo ........................ A61C 1/0046
                                                             433/29

* cited by examiner

DEVICE AND METHOD FOR SEPARATING A LONGITUDINALLY-EXTENDED CYLINDRICAL WORKPIECE

CROSS-REFERENCE TO RELATED APPLICATION

This is a continuation application, under 35 U.S.C. §120, of copending international application No. PCT/EP2013/060143, filed May 16, 2013, which designated the United States; this application also claims the priority, under 35 U.S.C. §119, of German patent applications No. DE 10 2012 211 206.5, filed Jun. 28, 2012 and DE 10 2012 212 718.6, filed Jul. 19, 2012; the prior applications are herewith incorporated by reference in their entireties.

BACKGROUND OF THE INVENTION

Field of the Invention

The invention relates to a device and a method for separating a longitudinally-extended cylindrical workpiece having a diameter in the sub-millimeter range into individual portions.

In particular in the manufacture of vessel supports, or stents, used in medicine, structural elements in the form of thin tubes having a diameter in the sub-millimeter range, for example between 100 and 300 µm, and a length in the millimeter range, which are precision-manufactured in a reproducible manner and the production of which is associated with significant technical issues, are required. For such structural elements a thin cylindrical workpiece, typically a hollow-cylindrical tube which is wound up on a supply roll and from which the individual structural elements have to be severed after prior additional processing, serves in the form of semi-finished product as the raw material. A particular production issue here is in particular the severing operation in which the portions forming the individual structural elements are severed from the optionally pre-processed workpiece.

A device for separating a hollow-cylindrical workpiece used in the manufacture of a stent into individual portions by a laser beam is known from published, non-prosecuted German patent application DE 10 2007 018 537 A1, for example, wherein the workpiece is guided in a guide body by way of a clamping force and wherein a free end of the workpiece which projects beyond this guide body is severed by the laser beam. Devices for manufacturing stents, in which a hollow-cylindrical semi-finished product is mounted in clamping devices for processing by a laser beam, are moreover disclosed in published, non-prosecuted German patent application DE 10 2008 011 232 A1 and in U.S. patent publication No. 2003/0234242 A1.

SUMMARY OF THE INVENTION

The invention is now based on the object of stating a device with which it is possible to economically manufacture structural elements of this type in large numbers. The invention is moreover based on the object of stating a method which is suited to the manufacturing of such structural elements.

With the foregoing and other objects in view there is provided, in accordance with the invention, a device for separating a longitudinally-extended cylindrical workpiece having a diameter in the sub-millimeter range into individual portions. The device contains a clamping device having at least one first and one second clamping jaw and an insertion opening for the workpiece. The workpiece is introduced in at least one of the clamping jaws on the side which faces the other clamping jaw. The clamping jaws have a longitudinal groove, which defines an indexing direction of the workpiece, for receiving and guiding the workpiece between the clamping jaws. The clamping device include an aperture for a laser beam and a cutting gas, which defines an operating zone and interrupts the longitudinal groove and runs transversely thereto. A cutting head is provided and has an exit opening for a laser beam and a cutting gas. The exit opening is aligned with the aperture and is disposed in the operating zone.

On account of the insertion opening which is located in the first and/or second clamping jaw, insertion of the workpiece into the longitudinal groove which is introduced into the first and/or second clamping jaw on that side which is in each case opposite to the opposing clamping jaw is facilitated.

Since processing of the workpiece is performed in an operating zone which, during processing of the workpiece by way of the laser beam and during impingement with the cutting gas, enables mounting of the workpiece on both sides of the aperture, precise processing of the workpiece, for example introduction of longitudinal slots, and also precise severing of small portions are both possible.

Moreover, when the aperture is simultaneously provided as the first outlet opening for the portions which have been severed from the workpiece by the laser beam and is connectable to a first receiving container by way of a flexible hose, secure and controlled handling of the severed short portions is ensured.

With respect to the method for separating a longitudinally-extended cylindrical workpiece into individual portions, the method includes the following steps:

a) inserting the workpiece into the insertion opening of the clamping device, b) indexing the workpiece until it bridges the aperture, c) performing a severance cut by a laser beam within the aperture, and d) drifting out the severed portion through an outlet opening which is aligned with the aperture, and onward conveying of the portion by the cutting gas through a flexible hose into a first collection container.

Since the workpiece is mounted on both sides of the aperture, precise processing and precise severing are both possible. Targeted drifting-out of the severed portion through the outlet opening and onward conveying of the severed portions by the cutting gas to a receiving container is also possible when the length of portion created hereby marginally exceeds the usable width of the aperture, since the portions tip into the aperture on account of the pressure exerted by the cutting gas.

Other features which are considered as characteristic for the invention are set forth in the appended claims.

Although the invention is illustrated and described herein as embodied in a device and a method for separating a longitudinally-extended cylindrical workpiece, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
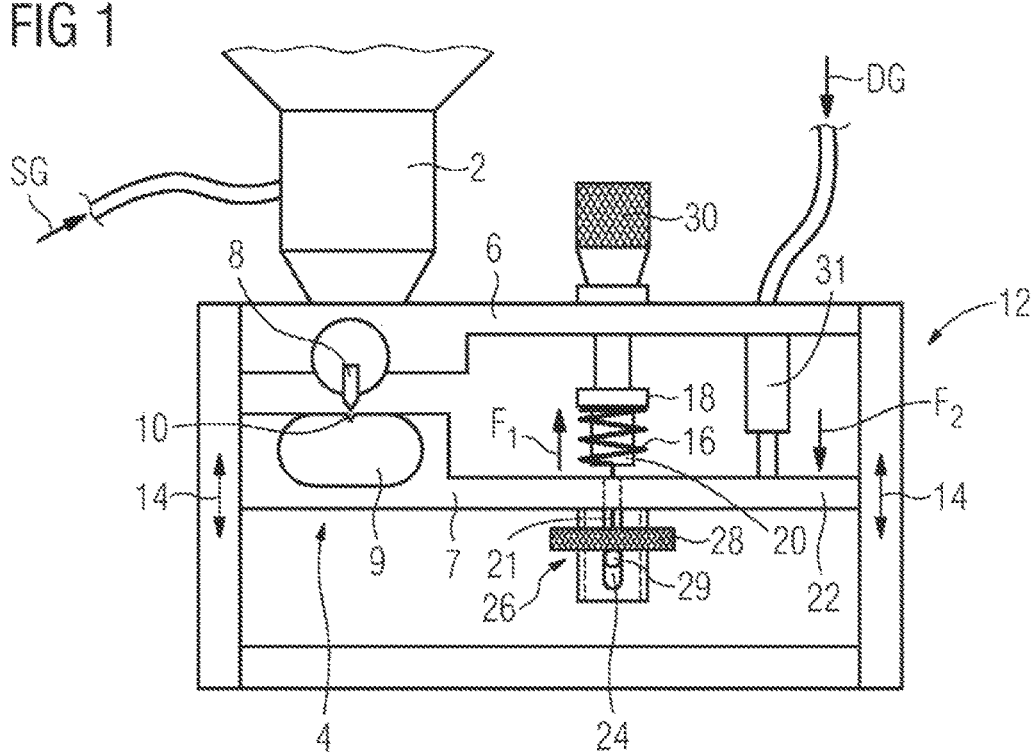
FIG. 1 is an illustration of a device for separating a longitudinally-extended cylindrical workpiece according to the invention.

Referring now to the figures of the drawings in detail and first, particularly to FIG. 1 thereof, there is shown a device having a cutting head 2 in which a laser beam generated by a non-illustrated laser-beam source is focused for cutting a workpiece 36 which is mounted in a clamping device 4. A cutting gas SG, with which the non-illustrated workpiece is impinged during cutting, is additionally supplied to the cutting head 2. The clamping device 4 has a first and a second clamping jaw 6 or 7, respectively, between which the thin cylindrical workpiece having an outer diameter in the sub-millimeter range, in particular a circular tube, composed of plastic or of a precious metal, having an outer diameter between 100 µm and 1000 µm, is received and guided. A first clamping body 8 is inserted into the first clamping jaw 6, and a second clamping body 9 is inserted into the second clamping jaw 7, which fixate or clamp the workpiece during processing in such a manner that said workpiece can still be axially displaced and rotated during processing.

In FIG. 1, the device is illustrated in a plan view onto that side of the clamping device 4 on which the workpiece is introduced through an insertion opening 10 between the first and second clamping jaws 6, 7, or, respectively, between the first and second clamping bodies 8 or 9, respectively, which are inserted into the first or second, respectively, clamping jaw 6 or 7, respectively.

The clamping device 4 is mounted in a frame 12, whereby in the illustrated exemplary embodiment the first clamping jaw 6 is rigidly mounted in the frame 12 and the second clamping jaw 7 is mounted in the frame 12 so as to be displaceable in the direction of double arrows 14, such that the second clamping jaw 7 can be closed toward the first clamping jaw 6. A pretensioned spring 16, in the example a helical spring which serves as a pull-spring, is disposed between the clamping jaws 6, 7, the pretensioning and accordingly the clamping force $F_1$ acting between the clamping bodies 8, 9 of the spring 16 being adjustable. In the illustrated example, the spring 16 is fixated at one of its ends on a flange 18 of a mandrel 20 which serves for axially guiding the spring 16. An opening, through which a rigid spacing element 21 which is connected to the other end of the spring 16 in a force-fitting manner is guided, is located in the second clamping jaw 7. A sleeve 26, which is provided with a thread and two longitudinal slots 24 which lie opposite one another, is disposed below the opening, onto which sleeve 26 a knurled nut 28 is screwed, a retaining pin 29 which is disposed on the spacing element 21 and protrudes through the longitudinal slots 24 engaging on the lower side of which knurled nut 28, such that a rough adjustment of pretensioning is enabled with the aid of the latter. For the fine adjustment of pretensioning, the flange 18 is connected to a micrometer drive 30 and can be axially adjusted by way thereof, such that a fine adjustment of the clamping force $F_1$ is enabled.

A lifting cylinder 31, pneumatically actuatable with pressure gas DG, by way of which it is possible to exert a counterforce $F_2$ which acts counter to the clamping force $F_1$ in order to facilitate insertion of the wire-type workpiece between the first and second clamping bodies 8, 9 is disposed so as to be parallel to the spring 16 between the clamping jaws 6, 7.

Figure 2:
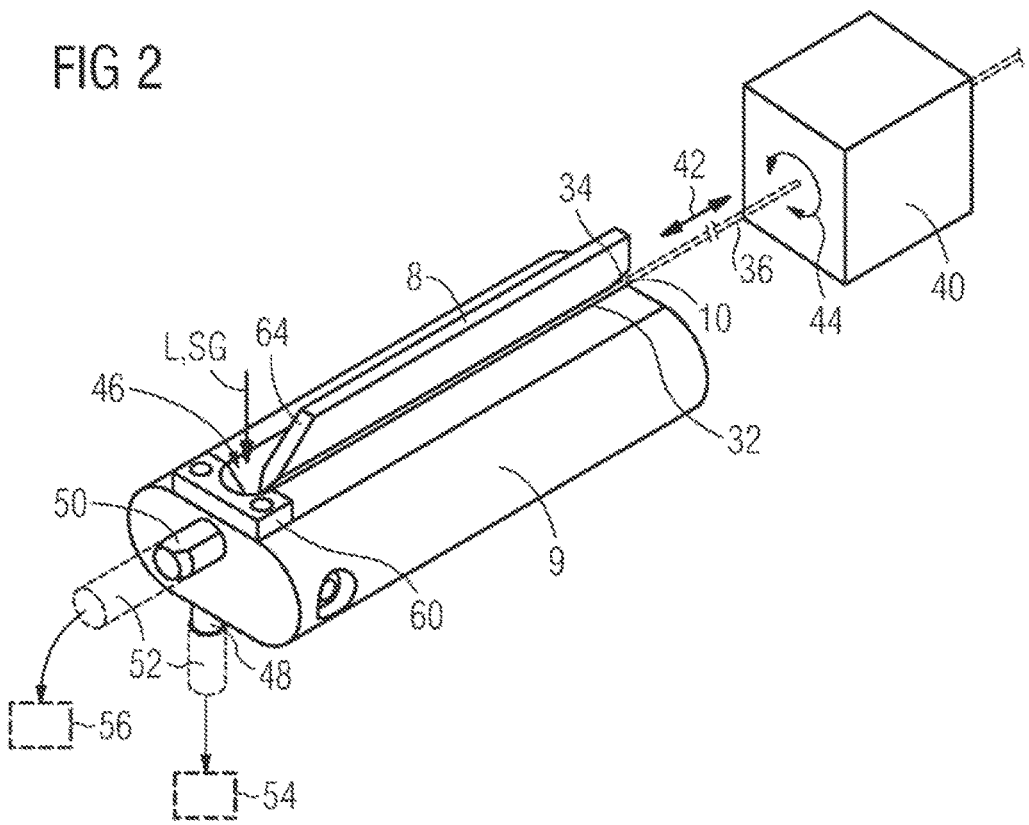
FIG. 2 is a diagrammatic, perspective view of components which serve as clamping bodies of a clamping device used in the device.

FIG. 2 shows the first and second clamping bodies 8, 9 (FIG. 1) which are in each case disposed in the first and second clamping jaws 6, 7, in a perspective illustration. It may be derived from FIG. 2 that the first clamping body 8 is formed by a strip which, on a narrow side which extends in a longitudinal direction, displays a cutting edge which in the cross section is V-shaped and by way of which the strip can be introduced into a longitudinal groove 32 which is located in the second clamping body 9 and which, in the cross section, is likewise V-shaped and which extends across the entire length of the second clamping body 9. The cutting edge, on its end, is flattened and displays a width which approximately corresponds to the diameter of the workpiece 36.

The strip, on its end which faces an insertion opening 10, is provided with an insertion ramp 34, such that the insertion opening 10, on account of a recess formed the insertion ramp 34 on the end face together with the longitudinal groove 32 which extends in the second clamping body 9 up to the end face, is enlarged, facilitating insertion of the thin cylindrical workpiece 36 into the longitudinal groove 32.

The workpiece 36 is fed to the first and second clamping bodies 8, 9 by a linear and rotary drive 40, by way of which the workpiece 36 can be moved to and fro along its longitudinal axis in the direction of double arrow 42, or can be rotated about its longitudinal axis in the direction of double arrow 44, respectively.

The first and second clamping bodies 8, 9 define a funnel-shaped operating zone 46, within which the workpiece 36 can be separated into individual portions by a static laser beam L while a cutting gas SG is simultaneously supplied. Additionally, a plurality of cuts or longitudinal slots which are distributed on the circumference may moreover be introduced into the workpiece 36 before it is separated into individual portions. During processing with the laser beam L, the workpiece 36 is rotated about its longitudinal axis during severing. Alternatively thereto, it is also possible for the severance cut to be performed by a movement of the laser beam L which is transverse to the longitudinal axis of the workpiece 36. Longitudinal slots which may be optionally required are introduced by axial displacement of the workpiece 36 prior to severing.

The first and second clamping jaws 6, 7, or the first or second clamping body 8, 9, respectively, which are inserted there into, are configured in such a manner that, when viewed in the indexing direction, they exert a clamping force on the workpiece 36 only up to an aperture 68 (FIG. 3) which is formed in the operating zone 46 for the laser beam 2 and the cutting gas SG.

Moreover, a first and second outlet opening 48 or 50, respectively, for the severed portions, which are in each case connected by way of a flexible hose 52 to a first or second, respectively, receiving container 54, 56, are located on the second clamping body 9 in the region of the operating zone 46. In this way, the severed portions are conveyed away from the operating zone 46 in a controlled manner. The hoses 52 are preferably composed of a metallic, tightly wound metal wire, in order to prevent an electrostatic charge and adhesion of the portions on the inner walls of the hoses 52 in particular when conveying portions composed of plastic.

A counter bearing 60 which displays a funnel-shaped recess 62 which tapers in a conical manner and forms half of a cone, is disposed opposite the strip on the second clamping body 9, so as to be able to position a likewise conically shaped cutting head 2 above the workpiece 36 at a spacing of only a few tenths of a millimeter between the exit opening and the workpiece 36. For this reason, an end side 64 of the first clamping body 8 which faces toward the operating zone is also shaped in an oblique manner.

Figure 3:
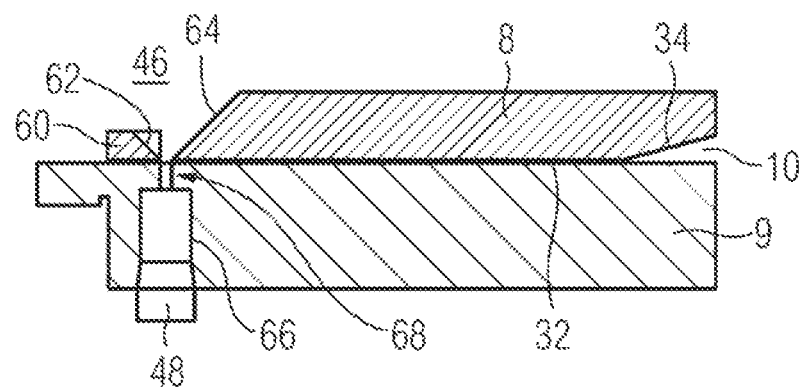
FIG. 3 is a longitudinal section view showing the clamping bodies illustrated in FIG. 2.

It may now be derived from FIG. 3 that the oblique end side 64 and the funnel-shaped recess 62, which is located in the counter bearing 60, align with a sequential bore 66 which is located in the second clamping body 9 and which forms the aperture 68 for the laser beam and the cutting gas in the clamping device 4. Accordingly, the counter bearing 60 is located beside the aperture 68, adjacent thereto on the side thereof which faces away from the insertion opening 10, and covers the longitudinal groove 32 which is located in the clamping body 9. Accordingly, the aperture 68 runs in a transverse manner to the longitudinal groove 32, interrupts the latter and is aligned with the exit opening 48.

Figure 4:
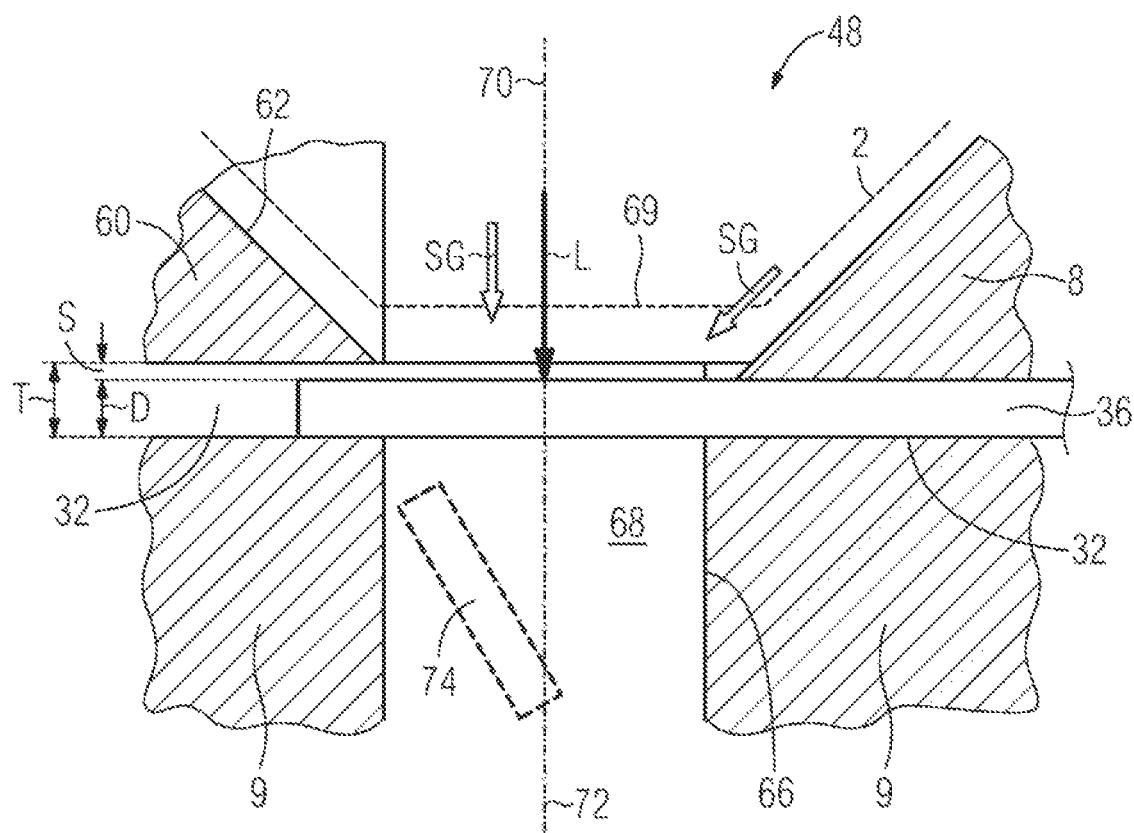
FIG. 4 is an enlarged longitudinal section view of the clamping bodies in a region of an aperture which is located in the clamping device.

The aperture 68 which is located in the operating zone 46 is illustrated in an enlarged manner in FIG. 4. In FIG. 4 the cutting head 2 which is inserted into the funnel-shaped operating zone 46 is moreover drawn using dashed lines, the exit opening 69 of which cutting head 2, through which the laser beam L and the cutting gas SG exit, is aligned with the aperture 68, whereby the central axis 70 of the cutting head 2 and the central axis 72 of the aperture 68 coincide.

FIG. 4 shows a situation in which the workpiece 36 has been indexed so far that, with its free end, it protrudes into the longitudinal groove 32, which is located below the counter bearing 60, and bridges the aperture 68. The diameter D of the workpiece 36 is smaller than a depth T of the longitudinal groove 32, such that a narrow gap s exists between the counter bearing 60 which is disposed on the second clamping body 9 and the workpiece 36.

Since during separating or processing the workpiece 36 bridges the aperture 68 and is not only fixated on account of the clamping force which acts between the first and second clamping bodies 8, 9, but moreover is supported at the free end by the second clamping body 9, deformation or sagging, respectively, of the workpiece 36 during processing by the laser beam is limited, such that the severance cut and also the longitudinal cuts can both be performed with high precision.

A severed portion 74 is automatically drifted downward out to the first outlet opening 48 (FIG. 2 and FIG. 3) by the cutting gas SG which flows into the aperture 68, and is fed through the hose 52 to the first receiving container 54 (FIG. 2). The counter bearing 60 which is located beside the operating zone 46 or beside the aperture 68, respectively, serves for reliably conveying comparatively long portions, which cannot be drifted out through the aperture 68, to the second exit opening 50, in order to feed the portions to the second receiving container 56. On account of the counter bearing 60 it is prevented that these comparatively long portions are blown away in an uncontrolled manner under the influence of the cutting gas SG. Where only short portions 74 are produced, the counter bearing 60 may also be dispensed with in principle.

In the exemplary embodiment, tubular portions 70, made of platinum Pt, having an outer diameter of 163 µm and a length of about 1000 µm, which are provided with a longitudinal slot on the circumference which extends across the entire length of the portion 70, are produced.

The invention claimed is:

1. A device for separating a longitudinally-extended cylindrical workpiece having a diameter in a sub-millimeter range into individual portions, the device comprising:
   a clamping device having at least one first and one second clamping jaw and an insertion opening formed therein for receiving the workpiece introduced in at least one of said first and second clamping jaws on a side facing the other of said clamping jaws, said clamping device having a longitudinal groove formed therein defining an indexing direction of the workpiece and for receiving and guiding the workpiece between said first and second clamping jaws, said clamping device having an aperture formed therein for a laser beam and a cutting gas and defining an operating zone and interrupting said longitudinal groove and running transversely to said longitudinal groove; and
   a cutting head having an exit opening formed therein for the laser beam and the cutting gas, said exit opening aligned with said aperture and disposed in said operating zone.

2. The device according to claim 1, further comprising:
   a flexible hose; and
   a first collection container, said aperture having a first outlet opening for the individual portions of the workpiece severed by the laser beam, and said first outlet opening connected to said first collection container by way of said flexible hose.

3. The device according to claim 1,
   wherein said first and second clamping jaws are configured such that said first and second clamping jaws exert a clamping pressure on the workpiece only up to said aperture; and
   further comprising a counter bearing covering said longitudinal groove and disposed in said clamping device beside said aperture, so as to be adjacent to said aperture on a side facing away from the insertion opening.

4. The device according to claim 2,
   further comprising a further flexible hose;
   further comprising a second collection container; and
   wherein said clamping device, opposite the insertion opening, has a second outlet opening formed therein for the individual portions which cannot be conveyed away through said first outlet opening, said second outlet opening connected to said second collection container by way of said further flexible hose.

5. The device according to claim 1, wherein said longitudinal groove is disposed in said second clamping jaw and in said longitudinal groove said opposite first clamping jaw has a strip which is insertable as one of said clamping bodies into said longitudinal groove.

6. The device according to claim 1, further comprising a frame, at least one of said first or second clamping jaws is mounted in said frame so as to be perpendicularly displaceable in relation to said longitudinal groove.

7. The device according to claim 6, further comprising an adjustably pretensioned spring for exerting a clamping force.

8. The device according to claim 7, further comprising a pneumatically actuatable lifting cylinder for exerting a counterforce acting counter to the clamping force exerted between said clamping jaws.

9. The device according to claim 1, further comprising a rotary and linear drive for rotating and indexing the workpiece and disposed upstream of said clamping device.

10. A method for separating a longitudinally-extended cylindrical workpiece into individual portions, which comprises the steps of:
  providing a device according to claim 1;
  inserting the workpiece into the insertion opening of the clamping device;
  indexing the workpiece until it bridges the aperture;
  performing a severance cut by the laser beam within the aperture; and
  drifting out a severed portion through an outlet opening aligned with the aperture, and onward conveying of the severed portion by the cutting gas through a flexible hose into a first collection container.

\* \* \* \* \*